United States Patent
Kollias et al.

(10) Patent No.: US 6,317,624 B1
(45) Date of Patent: Nov. 13, 2001

(54) APPARATUS AND METHOD FOR DEMARCATING TUMORS

(75) Inventors: Nikiforos Kollias, Watertown, MA (US); Jerome D. Fallon, Barrington, IL (US); Thomas J. Flotte, Boston; Jessica L. Fewkes, Belmont, both of MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 09/073,299

(22) Filed: May 5, 1998

Related U.S. Application Data

(60) Provisional application No. 60/044,025, filed on May 5, 1997.

(51) Int. Cl.$^7$ ............................................. A61B 5/00
(52) U.S. Cl. .................... 600/476; 600/477; 436/63
(58) Field of Search ........................... 600/407, 476–478; 436/63, 64

(56) References Cited

U.S. PATENT DOCUMENTS

| | | | |
|---|---|---|---|
| 4,930,516 | 6/1990 | Alfano et al. | 128/665 |
| 4,945,239 | 7/1990 | Wist et al. | 250/358.1 |
| 5,250,668 | 10/1993 | Morgan et al. | 540/145 |
| 5,413,108 | 5/1995 | Alfano | 128/665 |
| 5,419,323 | 5/1995 | Kittrell et al. | 128/653.1 |
| 5,421,337 | 6/1995 | Richards-Kortum et al. | 128/665 |
| 5,467,767 | 11/1995 | Alfano et al. | 128/665 |
| 5,590,660 | 1/1997 | MacAulay et al. | 128/664 |
| 5,647,368 | 7/1997 | Zeng et al. | |

FOREIGN PATENT DOCUMENTS

| | | |
|---|---|---|
| 2192036 | 4/1996 | (CA). |
| 0 765 673 A2 | 4/1997 | (EP). |
| WO/24360 | 6/1998 | (WO). |
| WO/46133 | 10/1998 | (WO). |

OTHER PUBLICATIONS

Andersson–Engels et al., "Fluorescense Diagnosis and Photochemical Treatment of Diseased Tissue Using Lasers: Part II", *Analytical Chemistry*, 62:19–27 (1990).

Cubeddu et al., "Optical Biopsy and Fluorescence and Imaging", *SPIE*, 2324:64–75, (1994).

Lohmann et al., "In situ Detection of Melanomas by Fluorescense Measurements", *Naturwissenschaften*, 75:201–202, (1988).

Lohmann et al., "In Situ Differentiation Between Nevi and Malignant Melanomas by Fluorescence Measurements", *Naturwissenschaften*, 78:456–457, (1991).

Lohmann et al., "Fluorescence Tomographical Studies on Breast Tissue with Cancer", *Naturwissenschaften*, 77:476–478 (1990).

Lohmann et al., "Native Fluorescence of Unstained Cryo–sections of the Skin with Melanomas and Nevi", *Naturwissenschaften* 76:424–426, (1989).

Andersson–Engels et al., "Fluorescence Imaging and Point Measurements of Tissue: Applications to the Demarcation of Malignant Tumors and Atherosclerotic Lesions from Normal Tissue", *Photochemistry and Photobiology*, 53:807–814, No. 6, 1991.

Harris et al., "Porphyrin Fluorescence and Photosensitization in Head and Neck Cancer", *Arch Otolaryngol Head Neck Surg*, 112:1194–1199, 1986.

(List continued on next page.)

*Primary Examiner*—Ruth S. Smith
(74) *Attorney, Agent, or Firm*—Fish & Richardson P.C.

(57) ABSTRACT

The invention features an apparatus and method for demarcating the margins of a tumor in a target tissue by exposing the target tissue to radiation of a wavelength that induces fluorescence in tumorous but not in non-tumorous tissue. A decrease in fluorescence indicates the presence of tumor cells.

20 Claims, 3 Drawing Sheets

OTHER PUBLICATIONS

Hung et al., "Autofluorescence of Normal and Malignant Bronchial Tissue", *Lasers in Surgery and Medicine*, 11:99–105, 1991.

Jazques, "Video Imaging With Polarized Light Finds Skin Cancer Margins Not Visible to Dermatologists", *Oregon Medical Laser Center News Etc.*, Feb. 1, 1998.

Newsletter, "Tumor Detection and Differentiation Possible with Ultra–Violet Light", *NCI Cancer Weekly*, Nov. 12, 1990, p. 4.

Svanberg et al., "Clinical Multi–colour Fluorescence Imaging of Malignant Tumors —Initial Experience", *ACTA Radiologica*, 39:2–9, 1988.

Zeng et al., "Miniature Spectrometer and Multi–spectral Imager as a Potential Diagnostic Aid in Dermatology", *SPIE*, 2387:57–61, Apr. 1995.

APPARATUS AND METHOD FOR DEMARCATING TUMORS

CROSS REFERENCE TO RELATED APPLICATIONS

This application claims priority from U.S. provisional application Serial No. 06/044,025, filed May 5, 1997, which is incorporated herein by reference.

FIELD OF THE INVENTION

The invention relates to the detection of the margins of tumors.

BACKGROUND OF THE INVENTION

Approximately one million new skin tumors, e.g., non-melanoma and melanoma tumors, are diagnosed each year in the United States. The treatment for most such tumors involves excising the tumor and a region of the skin surrounding the tumor. This so-called peritumoral region may contain tumor cells which have spread locally beyond the observable tumor. In addition to tumor cells, the peritumoral region may also include stroma that has been altered by the cells of the tumor, e.g., by tumor-mediated breakdown of components of the extracellular matrix. To determine the optimal amount of skin to remove, the treating physician typically makes a crude estimate, based upon a visual inspection of the tumor, and removes a corresponding section of the skin.

If the peritumoral region is underestimated, there is the possibility of tumor recurrence from tumor cells lying outside the excised area. Conversely, if the tumor region is overestimated, an unnecessarily large area of skin can be removed, and there is the possibility of unnecessary discomfort and disfigurement to the patient.

For a more precise measurement of the peritumoral region, the treating physician may perform Mohs micrographic surgery (MMS), in which horizontal sections of the region surrounding the excised tumor are examined microscopically for the presence of tumor cells. If tumor cells are detected, then additional skin is removed. MMS can be technically complex and also time consuming because of the time required to process and analyze the samples.

SUMMARY OF THE INVENTION

The invention is based on the discovery that endogenous fluorescence at excitation wavelengths of about 340 to 400 nm is almost entirely suppressed within, and in the immediate vicinity of, basal and squamous cell carcinomas. Accordingly, the invention provides a method of non-invasively detecting the margins of skin tumors by monitoring suppression of dermal fluorescence.

In general, the invention features a method for detecting the margin of a tumor in a target tissue, e.g., skin containing a skin tumor, by (a) exposing the target tissue to incident radiation at a wavelength of about 340 to about 400 nm, e.g., 330 to 410 nm, 350 nm to 400 nm, 360 to 380 nm, or 365 to 375 nm, that induces normal tissue but not tumorous tissue to emit fluorescence; and (b) detecting fluorescence emitted upon irradiation with the incident ultraviolet radiation, wherein a decrease in fluorescence compared to fluorescence emitted from normal tissue indicates the margin of a tumor within the target tissue.

The method can be used on tissues such to as skin, where it can be used to diagnose skin tumors such as basal cell and squamous cell carcinomas.

The method can be carried out by measuring the target tissue in a patient, e.g., any mammal, e.g., a human, dog, cat, or horse, in vivo, or by excising the target tissue from a patient and measuring the tissue in vitro.

The invention also features a method for detecting the breakdown of cross-linked collagen fibers in a target tissue, e.g., skin, by (a) exposing the target tissue to incident radiation at a wavelength that induces normal tissue but not tissue containing non-crosslinked collagen to emit fluorescence; and (b) detecting fluorescence emitted upon irradiation with the incident radiation, wherein a decrease in fluorescence compared to fluorescence emitted from normal tissue indicates the breakdown of collagen fibers within the target tissue, e.g., as associated with a skin tumor, skin atrophy, or with the formation of scar tissue.

In another aspect, the invention features an apparatus for detecting the margin of a tumor in a target tissue. The apparatus includes (a) an ultraviolet light source that irradiates the target tissue at a wavelength, e.g., 340 to 410 nm, that induces normal tissue but not tumorous tissue to emit fluorescence; (b) a detector to detect fluorescence emitted from the irradiated target tissue, e.g., at a wavelength of 420 to 480 nm, wherein a decrease in fluorescence compared to fluorescence emitted from normal tissue indicates the margin of a tumor within the target tissue; and (c) an element for suppressing blood flow in an irradiated area. The element can be an optical element e.g., a concave optical element.

By "tumor margin" is meant the region surrounding a tumor in which the stroma has been altered by the tumor. The tumor margin thus includes tumor cells that have grown beyond the edge of the tumor visible to the naked eye and also stromal regions that have been altered due to the presence of the tumor.

The invention has many advantages. In particular, the new methods provide a non-invasive, rapid, and accurate way to determine tumor margins. In addition, the methods provide a way for rapidly identifying the margin of a tumor in unstained histological sections of fresh tissue specimens in vitro, such as those obtained in MMS.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

The invention provides an apparatus and methods for non-invasively determining the margins of a skin tumor. This is accomplished by irradiating an area of skin within and surrounding the skin tumor with UV light at about 340 to about 400 nm and observing the emitted fluorescence. A decrease in fluorescence compared to normal tissue indicates the presence of tumor cells or alterations of the extracellular matrix associated with the presence of tumor cells, and thus the tumor margin can easily be determined.

In particular, applicants have discovered that when skin containing basal cell or squamous cell carcinomas is irradiated with light centered at approximately 370 nm, e.g., 340 to 410 nm, not only is fluorescence from the tumors significantly decreased compared to normal tissues, but fluorescence from a peritumoral region surrounding the tumor is also decreased. The peritumoral region showing decreased fluorescence is typically 2 to 3 times larger than the area of the tumor itself. Accordingly, fluorescence can be used to noninvasively define not only the tumor itself, but the tumor margin, as well. This is a significant advantage, since the tumor margin cannot otherwise be detected visually.

Fluorescence following excitation with UV energy at between about 340 and 400 nm, e.g., 330 nm to 410 nm, 355 to 400 nm, 360 to 380 nm, 365 to 375 nm, or 370 nm, can be used to define the tumor margins of skin cancers such as basal cell carcinomas and squamous cell carcinomas. Other tumors that can be assessed using the new methods include melanomas, skin sarcomas, such as fibrosarcomas, and skin metastases of tumors originating elsewhere in the body. In addition, fluorescence can be used to define tumor margins on tumors appearing on internal body organs as long as these tumors can be exposed directly to ultraviolet light, e.g., in a surgical procedure or via exposure through a fiber optic cable. In general, the method is useful for demarcating any tumors of tissues that include collagen. The method is particularly suitable for identifying margins in which tumor cells are degrading the structural matrix of the dermis.

Fluorescence of tissues induced by the specific UV wavelengths described herein can also be used to monitor cross-linked collagen fibers in patients suffering from collagen diseases. The decrease in emitted fluorescence correlates with the absence of cross-linked collagen fibers.

Apparatus for Detecting Dermal Fluorescence

Figure 1:
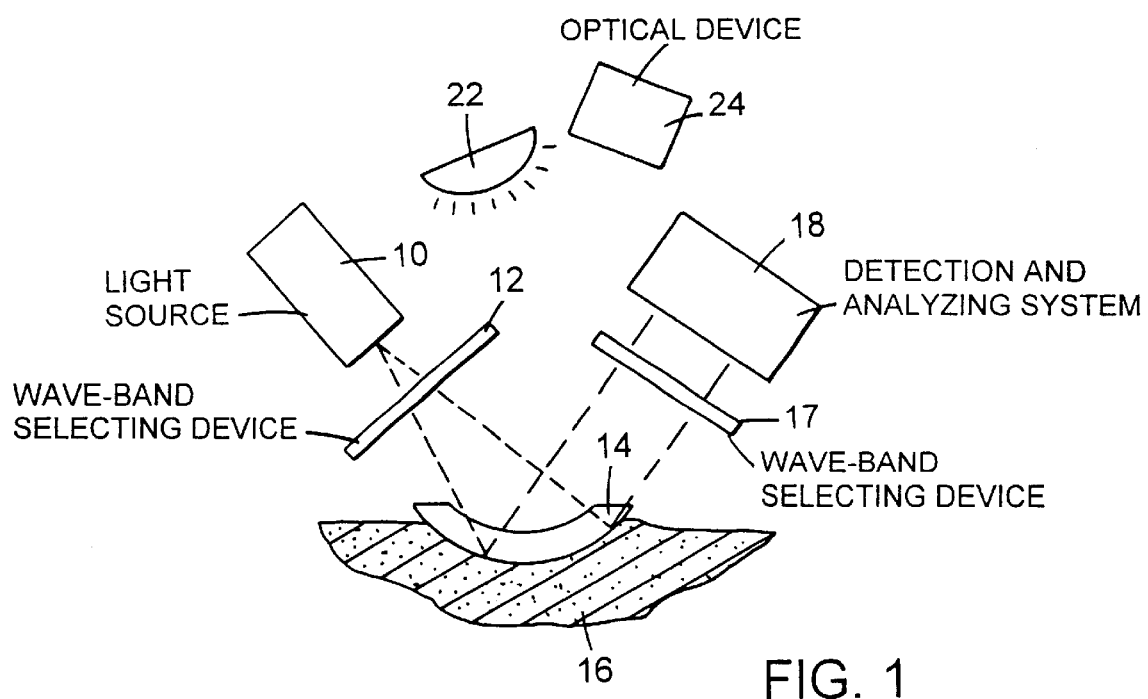
FIG. 1 is a drawing of the tumor demarcation apparatus.

As shown in FIG. 1, the apparatus includes a ultraviolet (UV) light source 10 for inducing fluorescence. In some embodiments, the light source is broad band and capable of emitting optical frequencies in the UV and near UV frequency range (200–450 nm). Accordingly, the light source 10 is optionally connected to a wave-band selecting device 12, e.g., a filter or a monochromator, which can be used to select optical frequencies from the broad band light source. The light source can have a band width on the order of 0.5 to 50 nm, e.g., 0.5 to 10 nm. Alternatively, the light source can be a uniband light source, or a tunable laser capable of emitting specific UV frequencies, such as an excimer laser or other lasers exciting in the same wavelength range.

The apparatus can optionally include an element 14 used to compress the blood vessels in the region of the target tissue 16 to exclude blood, thus avoiding fluorescence attenuation by hemoglobin. The element can be an optical element that is transparent to the excitation light, e.g., a concave optical element made of PYREX™ or quartz, through which the applied UV radiation will pass and which is brought in contact with the target tissue 16. The optical element is used with an optical coupling medium, such as water, a sugar solution, or mineral oil.

Following propagation through the monochromator or filter 12, or upon delivery from the uniband source 10, radiation is delivered to the target tissue 16. Radiation, e.g., fluorescence, emitted from the tissue passes through a second wave-band selecting device 17, e.g., a UV screening filter, which is used to prevent reflected excitation light from reaching the observer. The apparatus can additionally be connected to a detection and analyzing system 18 that stores and processes the filtered emission signal using standard equipment and techniques.

The apparatus may also optionally include a second, visible light source 22, e.g., a halogen lamp, which is preferably polarized, and an optical device 24, e.g., a camera, for visualizing the skin and recording the visual image of the skin.

In its simplest form, the device can be merely a UV light source that emits light at a wavelength of about 370 nm. Since skin illuminated by light in the vicinity of 370 naturally emits fluorescence in the range of 440 nm, which is visible, no detector is required. The user, e.g., technician, can merely illuminate the target tissue and observe where the natural fluorescence is attenuated, indicating the tumor and peritumoral tumor margin. For more precise measurements of the emitted fluorescence, a detection and analyzing system can be used.

Method of Detecting Dermal Fluorescence

Dermal fluorescence can be determined using one of the devices described above. The wavelength of the excitation energy applied to the skin is typically around 370 nm, e.g., 340 to 410 nm, 345 to 400 nm, 350 to 390 nm, 360 to 380 nm, or 365 to 375 nm.

In one embodiment, the excitation energy is applied in vivo, e.g., directly to a target tissue in the patient's skin (or tumor surface), e.g., a target tissue including a basal cell carcinoma or squamous cell carcinoma. The patient can be an animal, e.g., a mammal such as a person, dog, cat, horse, or cow. In another embodiment, the excitation energy is applied in vitro to a target tissue, e.g., a histological section of skin removed in MMS, and the resulting fluorescence is used to demarcate the tumor margin.

Because the emitted fluorescence maximum is near 440 nm, e.g., 400–480 nm or 420–460 nm, fluorescence can be monitored visually. The emitted radiation is optionally passed through a second wave-band selecting device, e.g., a UV filter, to protect the observer from reflected UV radiation. Alternatively, the emitted fluorescence can be detected using methods known in the art, e.g., by fluorescence microscopy using a OLYMPUS™ fluorescent microscope set at 10× magnification with a CCD digital camera. To detect low levels of emitted radiation, photon counting photomultiplier tubes, in conjunction with photon counting electronics, can be used. The image can be stored using imaging software known in the art.

If the fluorescence image is stored in a fixed medium, the image of the tumor and peritumoral region can be aligned to the region of skin containing the tumor using methods known in the art. For example, the fluorescence image can be aligned with a reference landmark or landmarks placed on the skin, e.g., fluorescent dyes placed on the skin. The landmarks on the skin can then be used to align the fluorescence image of the tumor and peritumoral region to the area of the skin tumor.

The fluorescence image can also be aligned to the skin by illuminating the skin with a visible light source in addition to the ultraviolet light. The fluorescent and visible light images can be fixed in some permanent form, e.g., transparencies, and this record can then be superimposed on the skin. The visible light source can be, e.g., a tungsten halogen lamp, and is preferably polarized.

However, the fluorescent image need not be stored, and can be observed in real time by the surgeon or technician. The tumor margin is then indicated on the patient's skin with a surgical pen or other marker, e.g., a fluorescent ink marker, following the edge of decreased fluorescence on the surface of the skin, just prior to removal of the tumor.

Tumor demarcation using fluorescence can be enhanced by distinguishing or eliminating signals from other substances that also absorb in the wavelength region of 370 nm. These substances include skin substituents such as hemoglobin, melanin, and keratin. Interference from hemoglobin can be suppressed by using a meniscus type optical element or surface that is pressed into the skin to expel blood and other fluids from superficial vessels. This optical device also minimizes the interference of signals from inflammatory lesions.

Interference from pigmented lesions such as those containing melanin can be minimized by comparing the image obtained with visible light with the fluorescent image. The interference from keratin, which can accumulate in the form of scales on the stratum corneum, can be suppressed by wetting the skin with water, e.g., with a wet gauze pad, for 5 to 10 minutes prior to imaging.

The fluorescence can also be influenced by the systemic presence in the patient of agents that fluoresce at excitation wavelengths around 370 nm. These agents can include polyaromatic compounds, certain antibiotics such as tetracycline, and certain vitamins such as vitamin B complexes. Accordingly, a patient should avoid ingesting such fluorescent compounds for one or more days prior to the procedure. Alternatively, the operator should take the extra fluorescence into account as background.

The invention will be further described in the following examples, which do not limit the scope of the invention described in the claims.

EXAMPLES

The following examples illustrate the use of fluorescence to identify skin tumors and peritumoral tumor margins surrounding skin tumors.

Example 1

In vivo Fluorescence of Normal Skin and of a Basal Cell Carcinoma at Excitation Wavelengths near 360 nm The fluorescence patterns of basal cell carcinomas and normal skin were first determined in vivo using a spectrophotometer essentially as described in Kollias et al., U.S. Pat. No. 5,456,260, except that the new wavelengths in the range of 300 to 400 nm were used. The spectrophotometer was set to the desired exciting wavelengths and was used to generate spectra noninvasively. A fiberoptic bundle transmitted the excitation light to the skin in a hand-held probe (Spex Industries), which also received the emitted light.

The source of the ultraviolet radiation was a xenon lamp and the ultraviolet radiation passed through a monochromator. The emitted light passed through a second monochromator, then a photomultiplier tube, after which the signal was processed and stored in a personal computer. For these experiments, excitation wavelengths of 250 to about 400 nm were used.

Figure 2A:
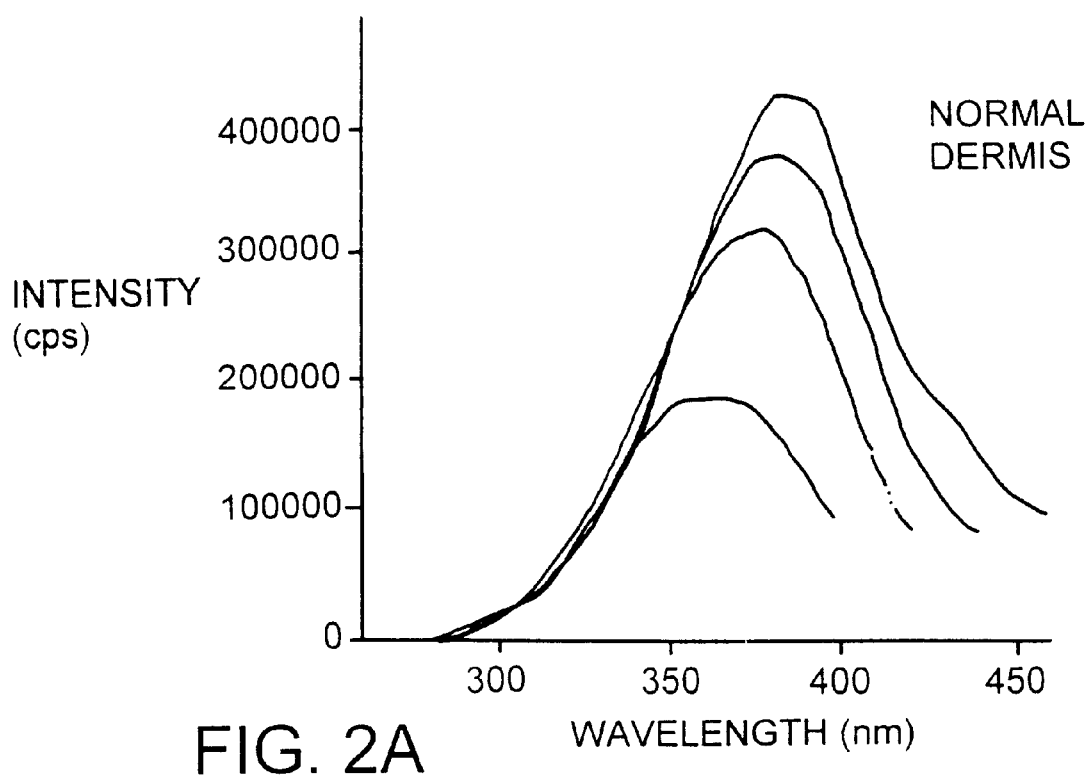
FIG. 2A is a graph showing a fluorescence excitation spectra of normal skin measured at four different emission wavelengths.
Figure 2B:
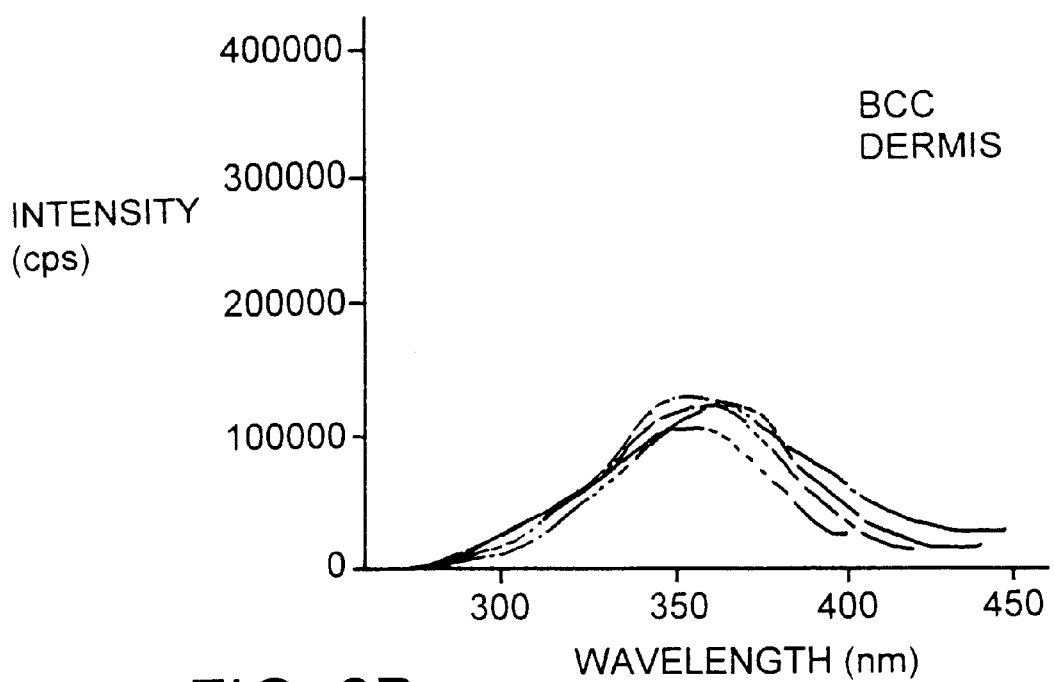
FIG. 2B is a graph showing a fluorescence excitation spectra of a basal cell carcinoma measured at four different emission wavelengths.

The intensity of the resulting emission radiation at four predetermined wavelengths from normal skin and from a basal cell carcinoma of a single individual are shown in FIGS. 2A and 2B, respectively. The spectra show the detected emitted fluorescence intensity at set wavelengths of 420, 440, 460, and 480 nm. As revealed by the comparative fluorescence profiles, the basal cell carcinoma (BCC) dermis tissue showed significantly less autofluorescence compared to that of the normal dermis tissue at excitation wavelengths around 360–370 nm.

Figure 3:
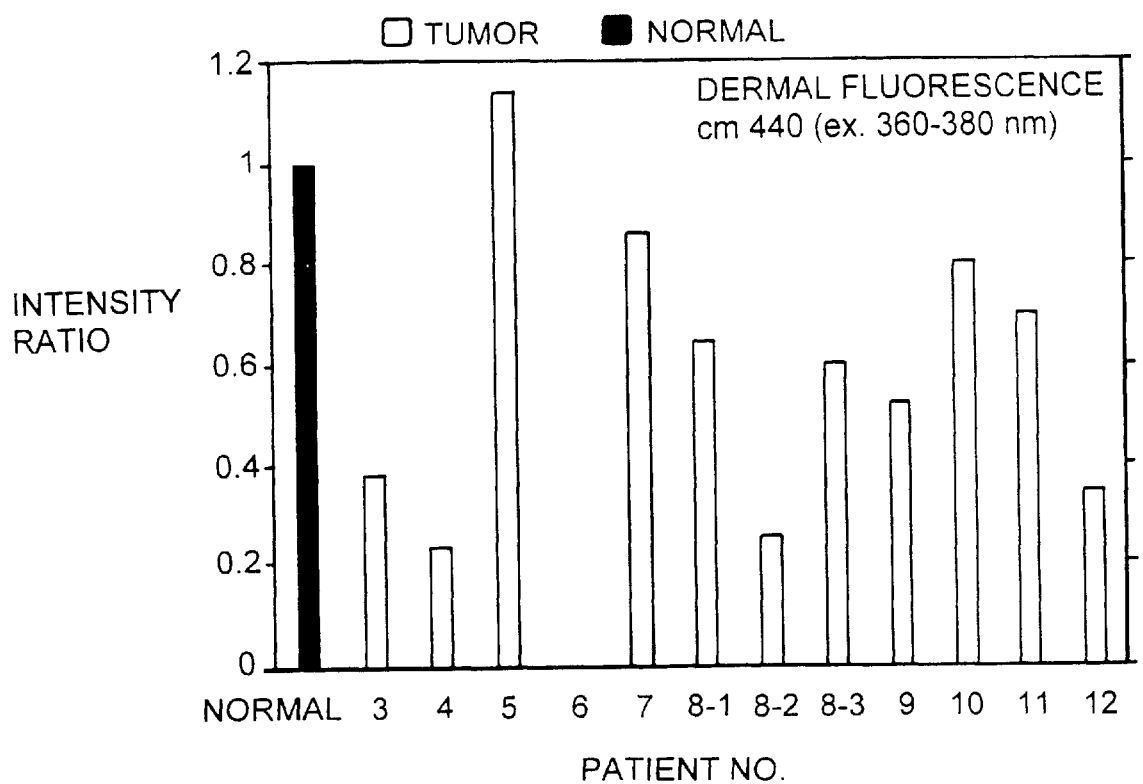
FIG. 3 is a histogram showing the fluorescence in normal skin and in basal cell carcinomas upon exposure to UV light of 360–380 nm.

The emission fluorescence following excitation at 360–380 nm was further examined on normal skin and on 12 basal cell carcinomas from a total of 10 individuals. The results are shown in FIG. 3, which is a histogram presenting the ratio of the intensity of the fluorescence obtained in each tumor sample to the intensity observed in the normal skin sample. No data were recorded for one patient (Patient No. 6), who elected to withdraw from the procedure before it could be completed. Decreased dermal fluorescence was observed for all but one of the remaining tumors compared to the fluorescence in the normal skin. Overall, the fluorescence detected in the basal carcinoma cells was approximately 40% of the fluorescence emitted by normal skin.

It is likely that these measurements underestimate the actual decrease in fluorescence due to tumors because the probe used in these experiments irradiates regions containing both tumorous and non-tumorous cells, and the presence of non-tumorous structural matrix in a field of tumor cells will increase the fluorescent signal. This also may explain why one tumor (Patient No. 5) showed higher than normal fluorescence. For example, the region irradiated in this experiment may have contained a higher region of non-tumorous matrix, and/or additional chromophores absorbing in the 360–370 nm region.

Example 2

Decrease of Fluorescence in Peritumoral Regions of Basal Cell Carcinomas

To examine fluorescence patterns at the cellular level, fluorescence patterns from histological sections of skin cancers analyzed via MMS were compared to the tumor margins as determined using the new method. The tumor margins as determined by MMS made it possible to confirm that the margins determined based on visually observed fluorescence in vivo matched the tumor margins determined by MMS.

Histological sections were obtained using MMS. Control cases were tumor negative at stage I on a standard hematoxylin and eosin (H & E) preparation. Thirteen basal cell carcinomas and one squamous cell carcinoma from 12 patients were examined. Fluorescence microscopy was performed on unstained sections using a source producing excitation wavelengths of about 365 nm.

For all samples tested the actual tumor was non-fluorescent. An additional zone or margin of non-fluorescence surrounded all tumor sites previously identified on H & E sections. These "black hole" zones were 2 to 3 fold larger than the dimensions of the tumor itself. In most cases, the autofluorescence technique permitted tumor detection on unstained Mohs sections as accurately as light microscopy of standard H & E preparations. In addition, the fluorescence identified a larger tumor margin than that identified by H&E sections.

The histological sections analyzed in these experiments did not contain blood. Thus, these results suggest that the differences in fluorescence patterns between normal and cancerous tissue are not due to differential blood flow to the two tissues in vivo.

Example 3

Use of Fluorescence To Demarcate a Basal Cell Carcinoma Tumor Margin In Vivo

A region of skin containing a basal cell carcinoma tumor is subjected to incident ultraviolet radiation of 360–370 nm. Regions showing decreased fluorescence are identified by visually observing the emitted radiation. These areas of decreased fluorescence, demarcating the tumoral and peri-tumoral regions, can be correlated to the regions of the skin producing the image by marking the edge between normal and decreased fluorescence with a fluorescent dye marker or surgical pen. The line indicates the margin of the basal cell carcinoma.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for detecting the margin of a tumor in a target tissue, the method comprising:
   (a) exposing the target tissue to incident radiation at a wavelength of about 340 to 410 nm; and
   (b) detecting fluorescence emitted upon irradiation with said incident radiation, wherein a decrease in fluorescence compared to fluorescence emitted from normal tissue indicates the margin of a tumor within the target tissue.

2. The method of claim 1, wherein said incident wavelength is between 360 and 400 nm.

3. The method of claim 1, wherein said incident wavelength is between 360 and 380 nm.

4. The method of claim 1, wherein said tissue is skin, and the tumor is a skin tumor.

5. The method of claim 4, wherein said skin tumor is a basal cell carcinoma.

6. The method of claim 4, wherein said skin tumor is a squamous cell carcinoma.

7. The method of claim 1, wherein said target tissue is measured in a patient in vivo.

8. The method of claim 7, wherein said patient is a human.

9. The method of claim 1, wherein said target tissue is excised from a patient and measured in vitro.

10. A method for detecting a breakdown of cross-linked collagen fibers in a target tissue, the method comprising:
    (a) exposing the target tissue to incident radiation at a wavelength of about 340 to 410 nm; and
    (b) detecting fluorescence emitted upon irradiation with said incident radiation, wherein a decrease in fluorescence compared to fluorescence emitted from normal tissue indicates the breakdown of cross-linked collagen fibers within the target tissue compared to normal tissue.

11. The method of claim 10, wherein said cross-linked collagen fibers are in skin.

12. The method of claim 10, wherein the breakdown in the cross-linked collagen fibers is associated with a skin tumor.

13. The method of claim 10, wherein the breakdown in the cross-linked collagen fibers is associated with an accumulation of scar tissue.

14. The method of claim 10, wherein said incident wavelength is about 340 nm to about 400 nm.

15. An apparatus for detecting the margin of a tumor in a target tissue, the apparatus comprising:
    (a) a light source that irradiates the target tissue at a wavelength of about 330 to 410 nm;
    (b) a detector to detect fluorescence emitted from the irradiated target tissue; and
    (c) an element for suppressing blood flow in an irradiated area, wherein a decrease in fluorescence compared to fluorescence emitted from normal tissue indicates the margin of a tumor within the target tissue.

16. The apparatus of claim 15, further comprising a wave-band selecting device for restricting the light that irradiates the target tissue to a wavelength from about 340 to about 400 nm.

17. The apparatus of claim 16, wherein said wavelength is between 360 and 380 nm.

18. The apparatus of claim 15, wherein said element for suppressing blood flow is a meniscus type optical element.

19. The apparatus of claim 15, further comprising a wave-band selecting device for restricting the emitted radiation to a wavelength from about 400 nm to about 480 nm.

20. The apparatus of claim 19, wherein the wavelength is between 420 nm and 460 nm.

* * * * *